(12) United States Patent
Li et al.

(10) Patent No.: US 7,883,893 B2
(45) Date of Patent: Feb. 8, 2011

(54) METHOD TO ASSAY TEST SUBSTANCES

(75) Inventors: Min Li, Lutherville, MD (US); Haiyan Sun, Baltimore, MD (US); Sojin Shikano, College Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 1117 days.

(21) Appl. No.: 11/272,050

(22) Filed: Nov. 14, 2005

(65) Prior Publication Data

US 2007/0111262 A1 May 17, 2007

(51) Int. Cl.
*G01N 33/53* (2006.01)
(52) U.S. Cl. ..................................... 435/375
(58) Field of Classification Search .................. None
See application file for complete search history.

(56) References Cited

PUBLICATIONS

Haiyan Sun et al., Function recovery after chemobleaching (FRAC): Evidence for activity silent membrane receptors on cell surface, *PNAS*, Nov. 30, 2004, pp. 16964-16969, vol. 101.

M. Edidin et al., Measurement of Membrane Protein Lateral Diffusion in Single Cells, *Science*, pp. 466-468, vol. 191, 1976.

Eric AJ Reits et al., From fixed to FRAP: measuring protein mobility and activity in living cells, *Nature Cell Biology*, Jun. 2001, pp. E145-E147, vol. 3.

Daniel Axelrod et al., Lateral motion of fluorescently labeled acetylcholine receptors in membranes of developing muscle fibers, *Proc. Natl. Acad. Sci. USA*, Dec. 1976, pp. 4594-4598, vol. 12.

Jia Xu et al., High-throughput technologies for studying potassium channels-progresses and challenges, Drug Discovery Today:Targets, Feb. 2004, vol. 3, No. 1, pp. 32-38.

*Primary Examiner*—Michael Pak
(74) *Attorney, Agent, or Firm*—Banner & Witcoff, Ltd.

(57) ABSTRACT

Membrane proteins represent ~30% of the proteome of both prokaryotes and eukaryotes. Unique to cell surface receptors is their biogenesis pathway, which involves vesicular trafficking from the endoplasmic reticulum through the Golgi apparatus and to the cell surface. Increasing evidence suggests specific regulation of biogenesis for different membrane receptors, hence affecting their surface expression. A pulse-chase assay can be used to monitor function recovery after chemobleaching (FRAC) to probe the transit time of the cell surface receptors to reach the cell surface. This method distinguishes molecular density from functional density. The ability of the reported method to access the biogenesis pathways in a high-throughput manner facilitates the identification and evaluation of molecules affecting receptor trafficking.

37 Claims, 9 Drawing Sheets

METHOD TO ASSAY TEST SUBSTANCES

The present invention was made using funds from the U.S. National Institutes of Health, under grant numbers 2 RO1 NS33324, 1 RO1 GM58488, and 1 RO1 DK61580. The U.S. government retains certain rights under the terms of these grants.

TECHNICAL FIELD OF THE INVENTION

This invention is related to the area of membrane protein biogenesis. In particular, it relates to assays of transit of biomarkers to the cell surface.

BACKGROUND OF THE INVENTION

The rate of membrane receptor trafficking is critical for the steady-state level of surface expression and is tightly coupled to signaling events (1-3). Within a given molecule, such as $K^+$ channels, various trafficking sequence motifs have been identified that contribute to the specificity of trafficking behavior (4). For a given receptor, recent evidence suggests that the rate of trafficking may change according to the physiological state, such as during cellular aging (5). To assess the transit time from the endoplasmic reticulum (ER) to the cell surface, a conventional approach is to measure the time of ER-to-Golgi transition, which is thought to be the rate-limiting step. The remaining steps of biogenesis usually take a very short time, ranging from seconds to minutes (6). The ER-to-Golgi transition time usually is determined by pulse-chase labeling combined with monitoring a shift of molecular weight as a result of glycosylation. This technique has been particularly useful for studies to determine specific organelle transitions, such as a rate change from ER to Golgi by forward transport signals (7). However, for proteins with limited or no glycosylation, this approach is not applicable. Furthermore, many receptors and ion channels undergo a stationary step in their trafficking cascade after exiting from trans-Golgi and before cell-surface expression. For example, only a fraction of synthesized nicotinic acetylcholine receptor matures and expresses on the cell surface (8). The combination of different transport rates, maturation pathways, and posttranslational modifications warrants a more in-depth consideration of methods to directly monitor the rate by which a given receptor complex populates and/or repopulates the cell surface after exiting from the Golgi apparatus.

In addition to the ER-Golgi trafficking, one critical spatial transition underlying diverse biological activity is the regulation of protein expression on the cell surface (for review, see ref. 9). Fluorescence recovery after photobleaching (FRAP) was developed for imaging the movement of biological molecules in cells (10, 11). This method has been improved greatly with extensive use of genetically coded fluorophores, such as green fluorescent protein (GFP), providing a powerful means to address questions regarding protein localization, activity, interactions, and dynamics with living cells (12). This approach has high spatial resolution at the single-cell level. However, the combination of optic detection and the photobleaching methodology limits its applicability in certain areas, especially evaluation of global surface expression and coupling the imaging signal to functionality of targeted molecules.

There is a continuing need in the art to develop methods for assaying cell surface protein transit. The assays should be useful whether or not a protein is glycosylated. The assays should be suitable for distinguishing cell surface molecules in different states, including but not limited to distinguishing functional from non-functional cell surface molecules.

SUMMARY OF THE INVENTION

According to one embodiment of the invention a method is provided for measuring the recovery of an activity on a cell surface. The cell surface is treated with a chemical or biological agent to affect an activity of a first population of cell surface receptors located on the surface of the cell at time of treating. The activity of the cell surface receptors is changed from a first to a second state. The first state of the activity on the cell surface is subsequently detected to determine presence of a second population of the cell surface receptors. The second population is not present on the cell surface at the time of treating. The amount or rate of appearance of the second population of the cell surface receptors provides a measure of the recovery of the activity on the cell surface. Optionally, the cell surface receptors which are treated are located in a specific area of the cell surface which is accessible to the chemical or biological agent.

Another embodiment of the invention provides a method of evaluating a test compound for its effect on the recovery of a function on a cell surface. The cell is incubated in the presence of the test compound. The surface of the cell is treated with a chemical or biological agent to affect an activity of a first population of cell surface receptors located on the surface of the cell at time of treating. The activity is thereby changed from a first to a second state. The first state of the activity on the surface of the cell is detected to determine presence of a second population of the cell surface receptors. The second population is not present on the cell surface at the time of treating. Optionally, the cell surface receptors which are treated are located in a specific area of the cell surface which is accessible to the chemical or biological agent.

These and other embodiments, which will be apparent to those of skill in the art upon reading the specification, provide the art with methods for drug evaluation, for biological agent evaluation, for assessment of cell pathologies, and for assessment of cellular effects of genetic changes. Exemplary cell pathologies include infections by bacteria, parasites, and viruses.

BRIEF DESCRIPTION OF THE DRAWINGS

(FIGS. 2a and 2b) In $Rb^+$ influx (FIG. 2a) and efflux (FIG. 2b), 293 cells were transiently transfected with Kir2.1Y expression vector (■) or empty vector (●). Data obtained with 2.5 mM [2-(trimethylammonium)ethyl]methanethiosulfonate bromide (MTSET) treatments are shown as □ or ○. (FIG. 2c) $Rb^+$ efflux of 293 cells stably expressing Kir2.1Y channel with (□) or without (■) MTSET treatment was measured. (FIGS. 2d and 2e) Determination of MTSET treatment conditions. (FIG. 2d) $Rb^+$ efflux (%) of 293 cells stably expressing Kir2.1Y channel (filled bars) and mock 293 cells (open bars) were quantified after being treated in triplicates with 5 mM MTSET for 0, 2.5, 5 and 10 min at room temperature. (FIG. 2e) $Rb^+$ efflux (%) of 293 cells stably expressing Kir2.1Y channel (filled bars) and mock 293 cells (open bars) were quantified after being treated in duplicate with 0, 0.5, 1, 2.5 and 5 mM MTSET for 5 min at room temperature.

(FIG. 3a-3b) $K^+$ channel activity measured by $Rb^+$ efflux assayed at the indicated time periods. Results are for 293 cells stably expressing either Kir2.1 (FIG. 3a) or Kir2.1Y (FIG. 3b) channel after MTSET treatment (□), $Rb^+$ efflux of 293 cells stably expressing Kir2.1 channel without MTSET treatment (■) and mock 293 cells treated with (○) or without (●) MTSET. (FIG. 3c) Flow cytometry analyses of 293 cells stably expressing Kir2.1Y channel with MTSET treatment at different time points (0, 3, and 6 h) before staining with anti-HA antibody to quantify the surface expression of Kir2.1Y. FL, fluorescence intensity in a logarithmic scale. Events refer to the number of cells.

(FIGS. 4a-c) Activity recovery of Kir2.1Y stable cell line after MTSET treatment (□), $Rb^+$ efflux of Kir2.1Y stable cell line without MTSET treatment (■), and $Rb^+$ efflux of mock 293 cells after MTSET treatment (○) or without MTSET treatment (●). The recovery experiments were carried out at 15° C. (FIG. 4a), 22° C. (FIG. 4b), and 30° C. (FIG. 4c). All measurements were performed in triplicate as described in Methods. (FIG. 4d) Normalized recovery rates from 0 to 5 h at 15° C. (■), 22° C. (□), 30° C. (▲), and 37° C. (◇) (from FIG. 3a). The $Rb^+$ efflux of Kir2.1Y without MTSET treatment was set to 100%.

(FIG. 5a) We incubated 293 cells stably expressing Kir2.1Y (hatched bars) and mock 293 cells (open bars) with 1 μM BFA at 37° C. for 3 h after a 5-min MTSET treatment or without MTSET treatment. In control samples, neither MTSET nor BFA were added. Each column is the average of two samples. (FIG. 5b) Dose-dependent effect by BFA treatment. Results show 293 cells stably expressing Kir2.1Y that were incubated with BFA only (■), cells stably expressing Kir2.1Y that were treated with MTSET before incubation with BFA (□), mock 293 cells incubated with BFA only (●), and mock 293 cells treated with MTSET before incubation with BFA (○). All experiments were performed in duplicate with 3-h incubation. The $Rb^+$ efflux (%) is plotted against different concentrations of BFA at 37° C. before $Rb^+$ efflux assay.

DETAILED DESCRIPTION OF THE INVENTION

The inventors have developed a strategy in which the activity of targeted cell surface receptors is modified, inhibited, or changed. By monitoring replenished activity of the receptors after modification, inhibition, or change, the assay allows for determination of transit time for receptor recovery on the cell surface. The procedure is dubbed "function recovery after chemobleaching" (FRAC), although either chemical or biological agents can be used to accomplish the "bleaching." The methodology takes advantage of a modification strategy applicable to almost all cell surface proteins. The function or activity of the cell surface proteins can be any detectable readout, such as ligand binding, enzymatic activity, epitope accessibility, ion conduction, fluorescence, and other physical properties.

Figure 1:
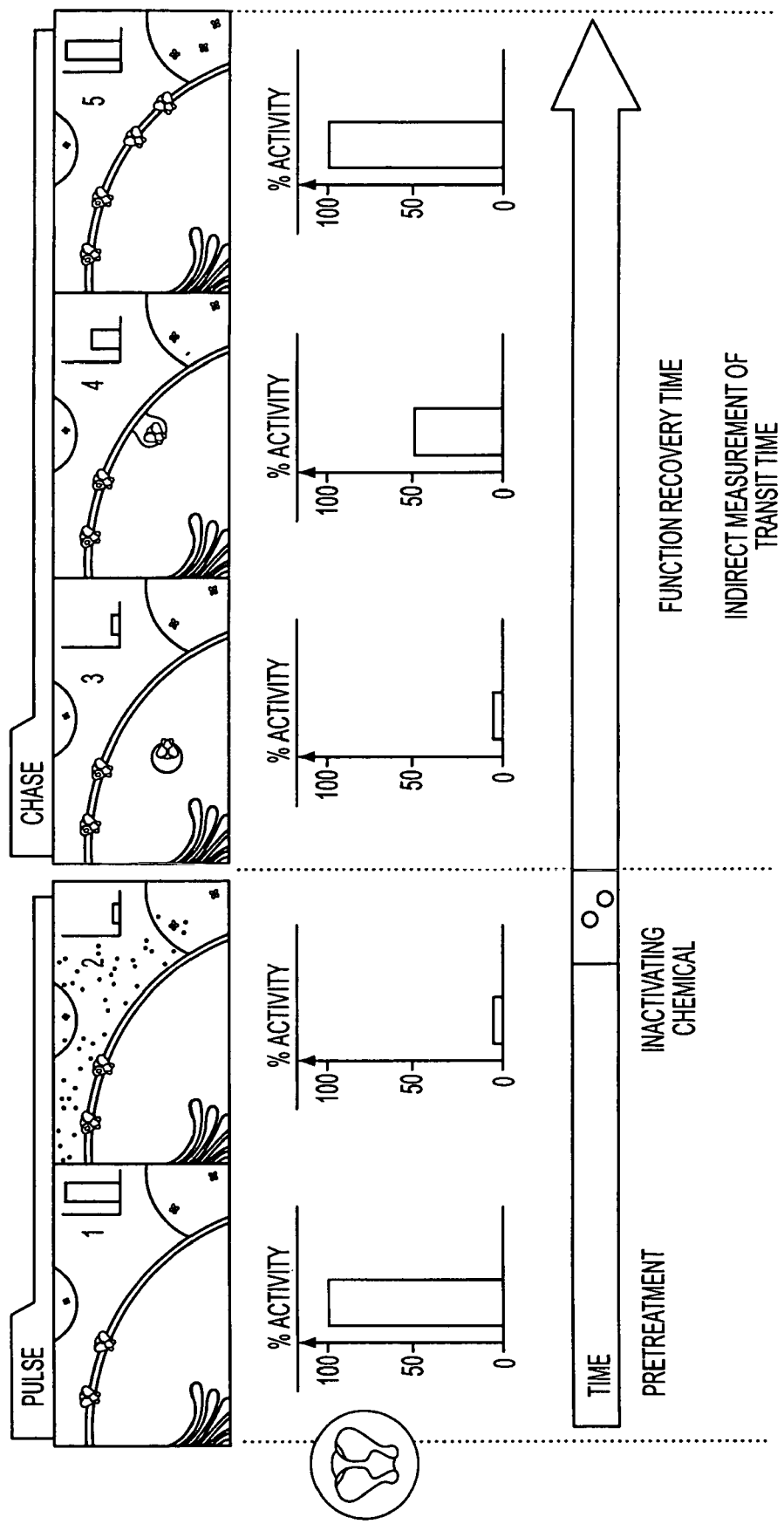
FIG. 1. A schematic diagram outlining the FRAC assay.

To assay the transit time of nacently surfaced receptor, we first modify, inhibit, or change (pulse) accessible functional molecules on the cell surface and then monitor the recovery of the original function/activity at subsequent time points (chase). One thus may determine the time required to populate the cell surface with newly inserted cell surface molecules (FIG. 1). Designing versions of this assay involves consideration of at least four factors. (i) A functional assay preferably monitors activity predominantly or only from molecules on the cell surface. (ii) Preferably the assay does not affect protein half-lives on the cell surface. (iii) The activity detection should be relatively short compared with the time required to repopulate the cell surface with functional molecules. (iv) The pulse should be rapid, quantitative, and optionally irreversible, thereby allowing detection of the activity contributed only by the newly arrived (or newly activated) proteins on the cell surface. These are considerations only, rather than mandatory properties. Deviation from one of these considerations may involve compensation by another. Furthermore, one of ordinary skill in the art will appreciate that treatment of cell surfaces can be restricted to a desirable area, such as the apical surface of epithelial cells. Thus, spatially restricted populations of cell surface receptors can be affected.

The activity or function on the cell surface which is monitored exists in two states. The first state is before the treatment with a chemical or biological agent and the second state is after treatment. The two states differ in magnitude or quality. For example, the second state may be an inhibited form, which is less active or exhibits no activity. The second state may have an altered activity, such as a change in binding properties from one ligand or substrate to another. Alternatively, the binding properties may change so that ligand or substrate binding becomes more or less selective. Another option is that the first and second states may differ epitopically, i.e., they are differentially bound by an antibody. In another option, the second state of the cell surface receptor may be more active then the first state. In another alternative, the second state results in a different subcellular location or a different oligomerization state. For example, in the second state the cell surface receptor may be internal to the cell.

Chemical or biological agents for treating the cell surface to effect a change in state of a receptor's activity or function can be any known in the art. The agents may bind or react reversibly or irreversibly with the cell surface receptor. The agents may covalently modify the cell surface receptor. The agents do not, however, destroy the cells or compromise the integrity of the cells. Thus the agents only have access to proteins which are external (on the cell surface) at the time of treatment. The agents may be toxins, antibodies, or pharmaceutical agents. Reactive agents such as mercury, diazonium ions, and dyes can be covalently linked to dextran to render them nonpermeant to cells and thus reagents suitable for treating cell surfaces. Suitable agents include methanethiosulfonates, including 2-trimethylammoniumethyl methanethiosulfonate bromide. Pore blockers such as teteraethylammonium can be used for potassium channels, and MK801 can be used for NMDA (glutamate) receptors. Agents which bind to, but do not block, pore-forming proteins can also be used.

In one particular assay, the biological agent is an antibody which specifically binds to a cell surface receptor. The same or a different antibody to the cell surface receptor is used to detect the second population of cell surface receptors. The antibodies, whether the same or different, can optionally be differentially labeled so that first and second populations are readily distinguishable. Alternatively, an antibody can be used in an assay of the first and second state. For example, a chemical agent may modify one or more residues in an epitope. The antibody can then be used to detect the original (first state) or the modified (second state) epitope.

The cell surface receptor may, for example, be a specific ligand binding receptor or may be an ion channel. Assays for the binding of ligand or for the uptake of the ion can be performed as are known in the art. Any means of detecting the activity of the cell surface receptor can be used. Preferably the detection will be relatively quick compared to the transit time of the receptor and/or compared to the time that the first population of cell surface receptors remains in the second state. As discussed below, if potassium ion channels are being assayed, a rubidium ion flux assay can be performed. Potassium channel activity can be measured by other means including voltage-sensitive dyes, fluorescence, and conventional electrophysiological recordings (15).

The cell surface receptors may be native to the cell or they may be introduced by recombinant means from the same or a different species. The receptors may be mutant, engineered, or wild-type. Examples of receptors which can be used are $K^+$ channels, Kir2.1 channels, Kir2.1Y, channels, HERG channels, $Ca^{2+}$ channels, $Na^+$ channels, glutamate channels, and $Cl^-$ channels. The receptors which are assayed may form a homogenous population or may be heterogeneous, i.e., comprising two or more types with similar or coordinated functions.

The assay can be performed on two sets of cells which differ in one or more aspects, and the results can be compared. The two sets of cells can be, e.g., from a normal and a diseased or pathological sample. The two sets of cells can be, e.g., a parental type (wild-type) and a genetically modified type. The genetic modification can be, for example, a mutation, an additional gene or copy of a gene, a viral infection, a bacterial infection, a recombinant gene, etc. Alternatively, the two sets of cells can be subjected to two different environmental conditions. For example, one set of cells can be subjected to a chemical agent, a biological agent, radiation, or illumination, or to an environmental condition of a particular temperature, pressure, or cell density, and the effect of the environmental condition can be determined oh the recovery of the cell surface receptor function. Any chemical or biological agent can be tested. These can be purified compounds, mixtures of compounds, libraries of compounds, natural products, or synthetic products. They can be tested individually or in groups.

Cells used in the assays of the invention are any membrane enclosure which provides insulation to internal components from chemical and/or biological treatments. A cell may be a native or recombinant cell, and may be from any organism. A cell may be in a specific state, e.g., a sperm or an oocyte, a fusion product of more than one cell, an aggregation of identical or heterogeneous cells formed as the result of growth in culture or isolated from tissue, or a vesicle of insulated lipid layers. A cell may be from a particular organ such as heart, brain, kidney, liver, colon, skin, etc. Cells may be treated and assayed in vitro in cell culture or in vivo in whole animals.

Recovery of the function of the cell surface receptor (or the first state of the activity of the cell surface receptor) can be determined at a fixed time point, at multiple time points, or continuously. A rate can be determined or an amount of recovery at a fixed time point can be determined.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials. The methanethiosulfonate reagents, such as [2-(trimethylammonium)ethyl]methanethiosulfonate bromide (MTSET), were purchased from Toronto Research Chemicals (Downsview, ON, Canada). Brefeldin A (BFA), sodium butyrate, and RbCl were purchased from Sigma.

Transfection and Stable Cell Lines. Expression vectors were constructed using pcDNA3.1(+) (Invitrogen), and the Kir2.1 cDNA was cloned into HindIII and NotI sites. For the two Kir2.1 cDNA clones used in the study, one has the hemagglutinin (HA) epitope inserted at the first extracellular loop between M1 and P-loop to facilitate surface detection (13), referred to as Kir2.1. The other has both the HA epitope and a peptide, FRGRSWTY, fused at the C-terminus to facilitate surface expression, which is referred to as Kir2.1Y. The transfection into HEK 293 cells was carried out with FuGENE 6 (Roche Diagnostics). Stable clones were selected for neomycin resistance. Stable clones with high expression level of channel proteins were selected using immunoprecipitation and flow cytometry. These stable cell lines were maintained in 50/50 DMEM/F12 medium containing 10% FBS, penicillin/streptomycin, L-glutamine, and 500 µg/ml G418.

Flow Cytometry. HEK 293 cells stably expressing Kir2.1 or Kir2.1Y channel were seeded at $\sim 3 \times 10^5$ cells per well in a six-well plate and allowed to grow for 16-20 h in complete growth medium with 5 mM sodium butyrate at 37° C. and 5% $CO_2$. Cells were washed with 1×PBS and harvested by incubation with 0.5 mM EDTA in 1×PBS for 5-10 min at room temperature. Cells then were washed twice with Hanks' balanced salt solution (HBSS) plus 5 mM Hepes (pH 7.3) and 2% FBS and incubated with rat anti-HA monoclonal antibody (Roche Diagnostics) on ice for 1 h. Cells then were washed twice again with HBSS staining medium and incubated with FITC-labeled goat anti-rat IgG antibody (Jackson ImmunoResearch) for 15 min on ice. Finally, the cells were washed twice with HBSS staining medium, and the channel-surface expression was measured by FACSCalibur (Becton Dickinson) with CELLQUEST software (Becton Dickinson).

$Rb^+$ Flux Assay and Atomic Absorption Spectrometry. All assays shown were performed at room temperature in poly (L-lysine) (0.1 mg/ml)-coated 24-well microplates. For experiments with transiently transfected cells, $\sim 1 \times 10^5$ cells were seeded in each well the day before transfection (0.3 µg of DNA per well). Sodium butyrate at 5 mM was added 6-8 h after transfection. The assays were performed 24 h after transfection. HEK 293 cells stably expressing either Kir2.1 or Kir2.1Y channel were seeded with a cell density of $2 \times 10^5$ cells per well. To enhance expression, 5 mM sodium butyrate was added 4-6 h after seeding. Cells then were cultured continuously for 16-20 h before experiments.

$Rb^+$ Influx. To perform the assay, cells first were incubated in 50/50 DMEM/F12 complete growth medium containing 5 mM RbCl for the indicated time periods before the medium was quickly aspirated. Cells then were washed twice quickly with non-$Rb^+$ DMEM/F12 medium and lysed with 0.5 ml of 0.1% SDS per well. The $Rb^+$ concentration in cell lysates was measured by atomic absorption spectrophotometry (ICR8000, Aurora Biomed, Vancouver), according to the manufacturer's user manual.

$Rb^+$ Efflux. To load $Rb^+$ into cells, we incubated cells in 0.5 ml per well 50/50 DMEM/F12 complete growth medium containing ~5 mM RbCl at 37° C. for 3-4 h. Cells then were washed twice quickly with 1 ml per well non-$Rb^+$ medium to remove residual $Rb^+$. To perform the assay, 0.5 ml of non-$Rb^+$ complete growth medium per well was added to the cells, which were incubated at room temperature for 15 min unless otherwise indicated in the legends of FIGS. 1, 2, 3, 4, 5. The supernatants from each well were transferred quickly to a new 24-well plate at the end of incubation. Cells then were lysed with 0.5 ml of 0.1% SDS per well. The supernatants and cell lysates were diluted further with distilled water, and the diluted samples were transferred to a 96-well microplate. The $Rb^+$ concentration in each sample was analyzed using the ICR 8000. $Rb^+$ efflux (%) was determined as:

$$100\% \times [Rb^+]_{sup} / ([Rb^+]_{sup} + [Rb^+]_{lysate})$$

where $[Rb^+]_{sup}$ represents the $Rb^+$ concentration in the supernatant, and $[Rb^+]_{lysate}$ represents the $Rb^+$ concentration in the cell lysate.

Example 2

Kir2.1 encodes an inward rectifier $K^+$ channel consisting of four subunits that align to form a centrally positioned hydrophilic pore to conduct $K^+$ ions (14). One of the attractive features of the Kir2.1 channel is that it has an open probability of nearly 100% at resting potential, thereby permitting an option of monitoring the activity without depolarization. Assays for detecting $K^+$ channel activities include electrophysiological recording, fluorescence-based measurements, and $Rb^+$ flux assay (for review, see ref. 15). All three types of assays can be achieved within minutes. The primary distinctions concern whether the assay reads signals from individual cells or a population of cells and whether the cells remain intact during the entire assay procedure. We chose the $Rb^+$ flux assay because of its ability to assay a large population of cells for extended time periods without rupture of cell membrane. The flux activity linearly reflects the conducting ion passage. $Rb^+$ is a nonphysiological ion but is permeable to almost all $K^+$ channels, which affords general applicability. In addition, the $Rb^+$ assays described here were carried out under conditions that do not tamper with the membrane potential, hence avoiding a stimulation of membrane fusion that could be caused by depolarization-induced $Ca^{2+}$ influx.

To modify, nullify, or change the $K^+$ channels already expressed on the cell surface, several approaches have been considered. These include antibody binding induced inhibition (16), pore blockers (such as tetraethylammonium), and covalent modifications by, for example, methanethiosulfonate (MTS) reagents (17). Of the three possibilities, covalent modification is advantageous because MTS reagents are irreversible under typical physiological redox conditions and would not cause clustering that often leads to other subsequent events, including endocytosis. Other reagents may be preferred for other cell surface receptors or applications.

Earlier reports using electrophysiological recording have shown that membrane-nonpermeable MTS reagents such as MTSET reduce or abolish the current of Kir2.1 by covalently modifying the reduced form of cysteine residues already present in the channel protein or introduced by site-directed mutagenesis (18). It is not known whether or to what extent the modifications by MTS reagents will affect channel activity measured by a $Rb^+$ flux assay. We tested several cysteine positions of Kir2.1 mutants using MTSET, a positively charged cysteinyl sulfhydryl-specific reagent. Our results show that wild-type Kir2.1 may be quantitatively nullified by MTSET. Notably, a mutation of C149, the only cysteine on the extracellular side, leads to a loss of sensitivity to MTSET both by electrophysiological recording and $Rb^+$ assay (data not shown). This data is consistent with results from electrophysiological recording (18), further confirming the fact that MTSET acts on the extracellular cysteine at the 149 position.

Figure 2A:
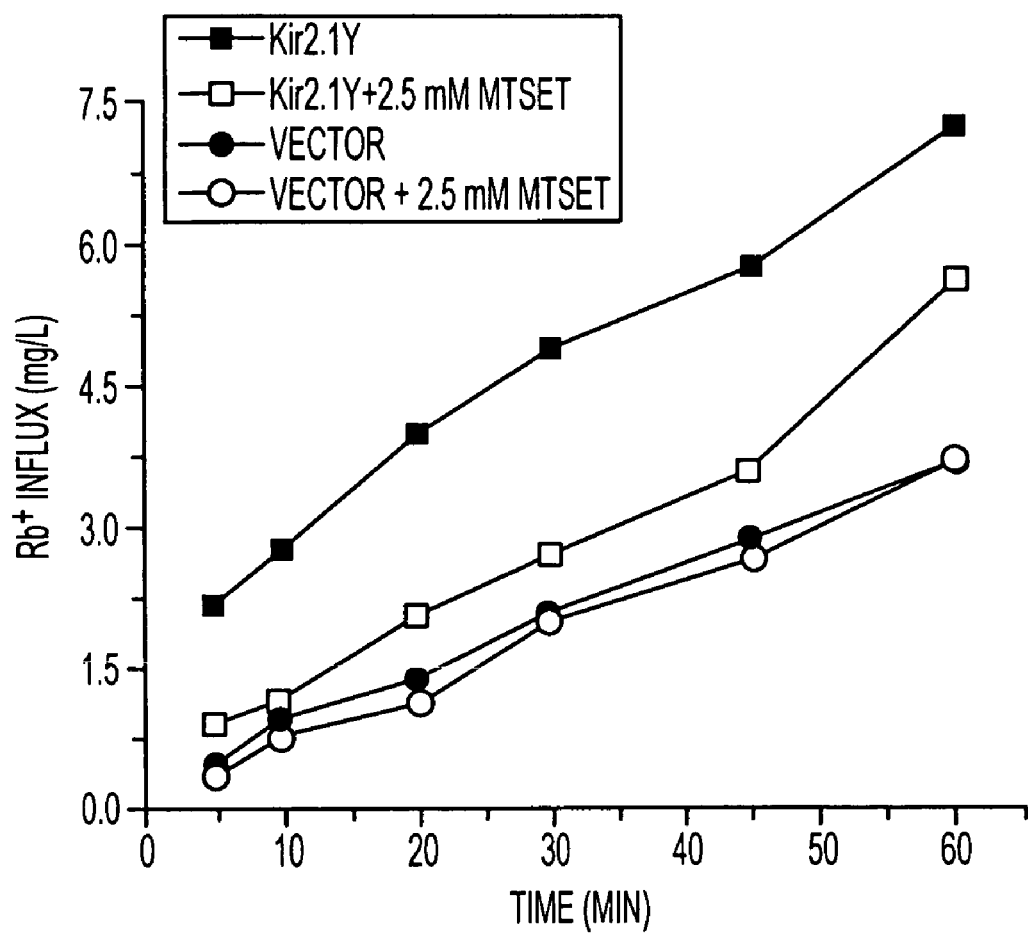
FIGS. 2a-2e. $Rb^+$ flux assays of HEK 293 cells transiently and stably expressing Kir2.1Y channel.
Figure 2B:
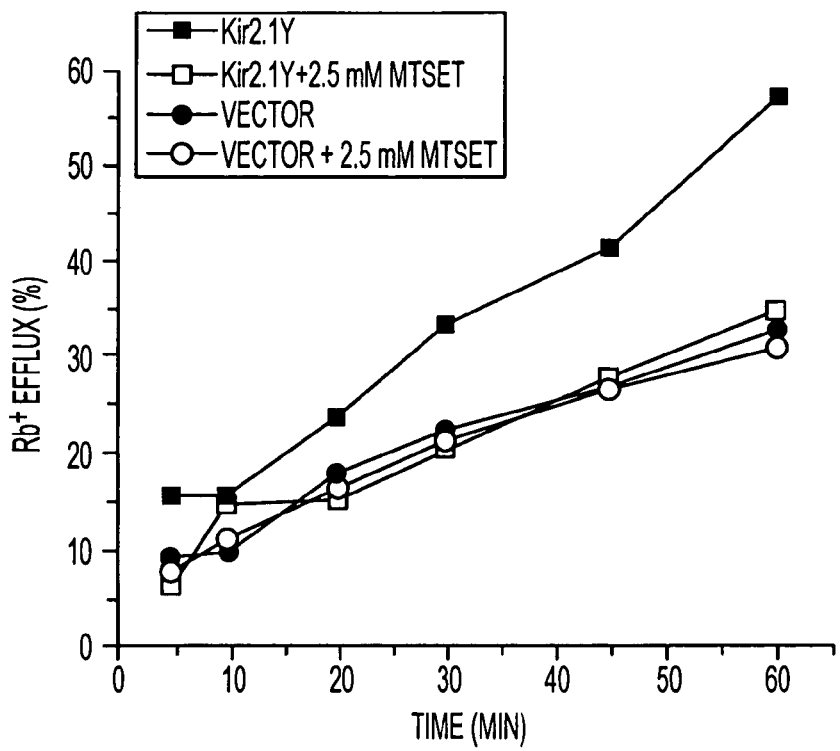
Figure 2C:
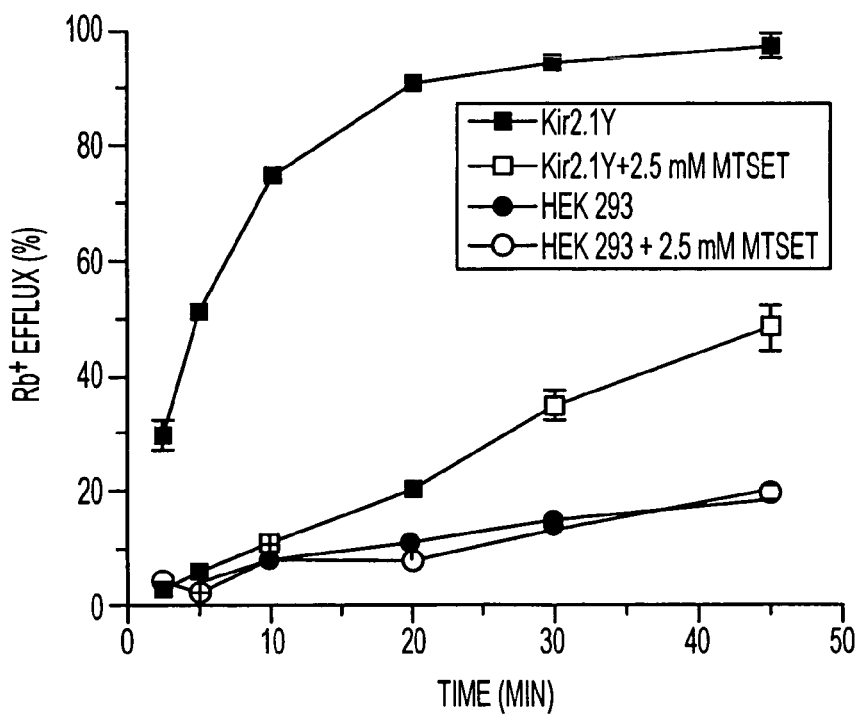
Figure 2D:
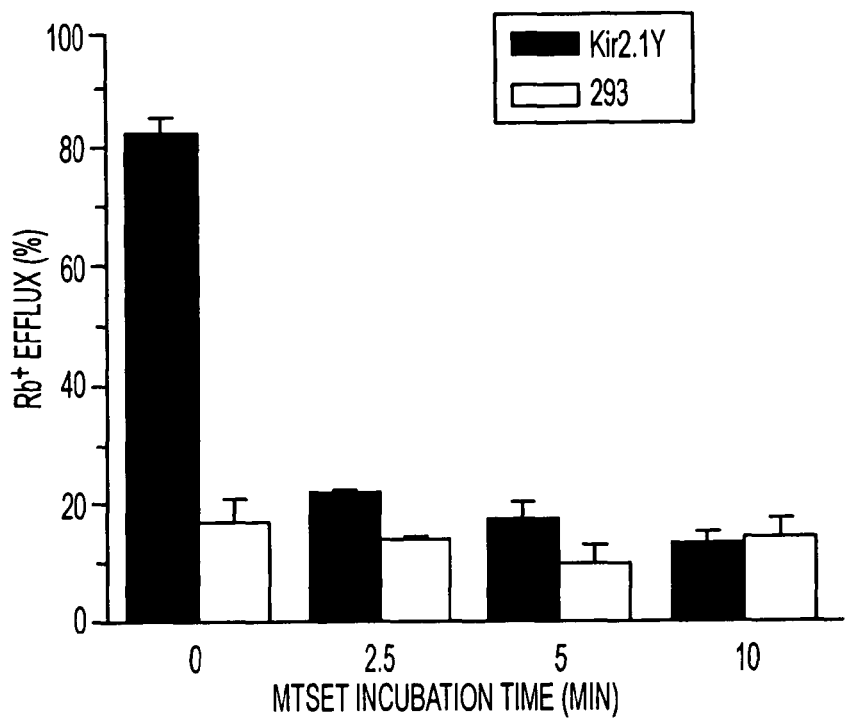
Figure 2E:
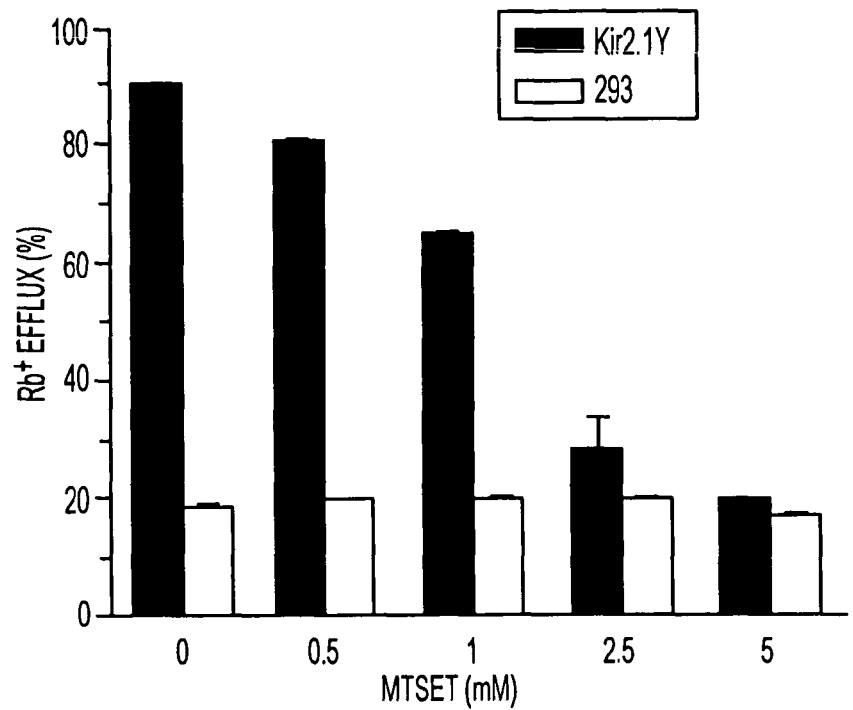

To monitor the specificity of the $Rb^+$ assay and the effectiveness of $Rb^+$ detection by atomic absorption spectrometry (19), we measured the $Rb^+$ uptake signals of transiently transfected cells at different times of incubation. Comparison of transfected cells with nontransfected cells revealed an ~2-fold signal-to-noise ratio (FIG. 2a) in a 10-min uptake. Treatment with MTSET before the assay abolished >80% of the specific signal. Prolonging uptake time increased the total signal but did not improve the signal-to-noise ratio. It should be noted that the influx measures the absolute level (mg/L) of $Rb^+$ inside the cell. Thus, it is also a function of cell number in a given assay and dependent on $Na^+$—$K^+$ ATPase. We then compared the uptake (i.e., influx) with the efflux assay, which reflects the ratio of $Rb^+$ released in the supernatant to total $Rb^+$ in the loaded cells (see Methods and FIG. 2b). To further improve the signal-to-noise ratio, cell lines were generated that stably express either the Kir2.1 or Kir2.1Y channels (see Methods). The efflux assay using a stable Kir2.1Y line displayed a significant improvement of a nearly 4- to 6-fold signal-to-noise ratio (FIG. 2c). When cells were treated with MTSET, only background signals were observed. To determine the optimal conditions, we performed a titration using different concentrations and time courses of the MTSET treatment. The results suggest an optimal treatment with 2.5 mM MTSET for 5 min (FIGS. 2d and 2e). These results demonstrate the functional expression of Kir2.1 channels, the sensitivity of the $Rb^+$ efflux assay, and the feasibility of nullifying the channel activity on the cell surface by MTSET.

Example 3

Figure 3A:
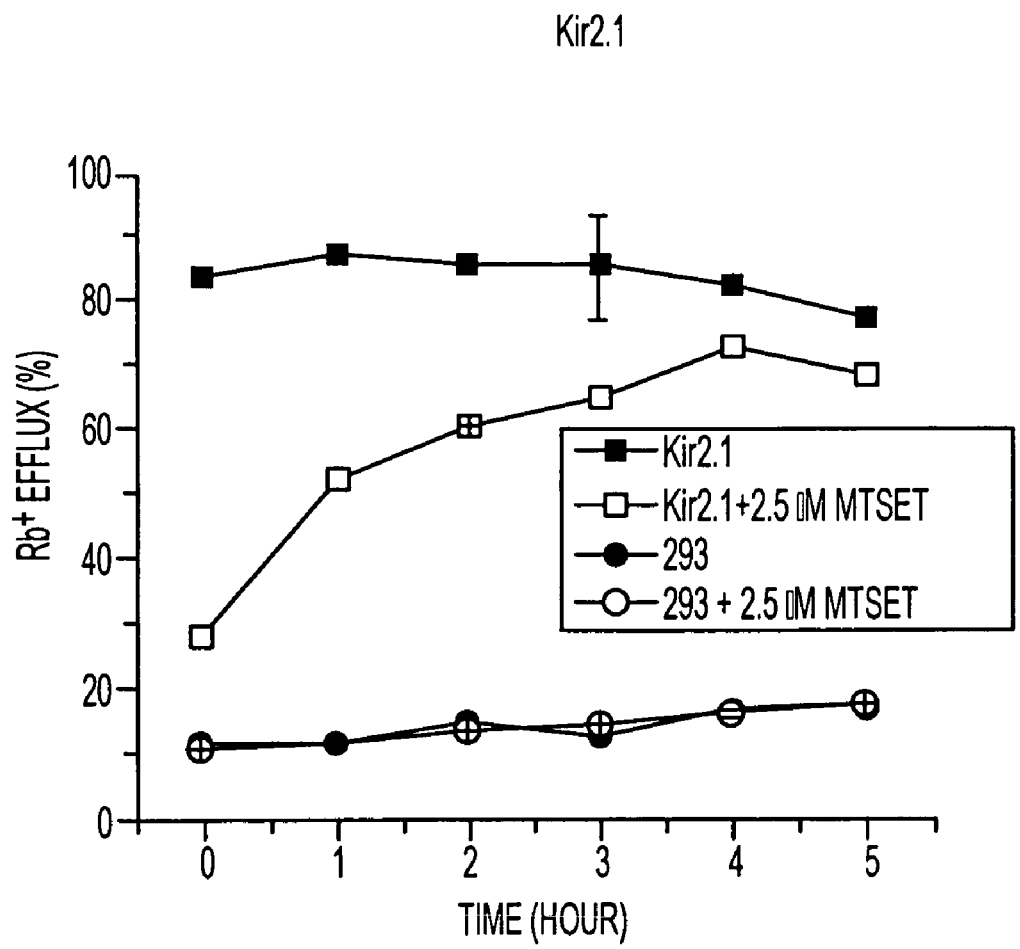
FIGS. 3a-3c. Detection of Kir2.1Y and Kir2.1 channel functional surface expression.
Figure 3B:
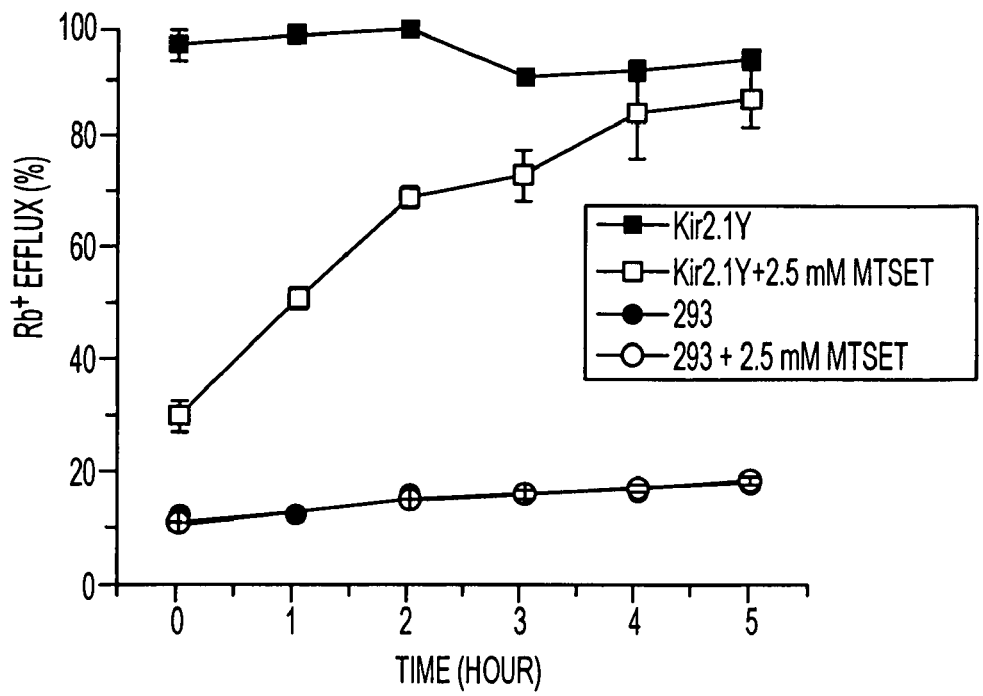

To evaluate FRAC, we generated two cell lines expressing either the Kir2.1 or Kir2.1Y where the protein expression level of Kir2.1Y is ~2-fold higher than that of Kir2.1 (data not shown). Both cell lines were treated first with MTSET to nullify the channels on the cell surface. After its removal, the treated cells were assayed after incubations of the indicated periods of time for recovery. The half-maximal functional recovery time ($FR_{1/2}$) at 37° C. for both Kir2.1 and Kir2.1Y was 1 h (FIG. 3a). The functional expression reached 90% of the initial level 5 h after chemobleaching with MTSET. During the chase period, the $Rb^+$ loaded cells without MTSET treatment gave rise to similar signals (FIG. 3a). The background $Rb^+$ efflux of nontransfected cells remained consistent with or without MTSET treatment (FIG. 3a). The result shows that recovery was specific to the cells expressing the recombinant channels. To monitor the level of Kir2.1Y protein on the cell surface, flow cytometry analyses were carried out using live cells stained with anti-HA antibody (see Methods). The total amount of protein signals remained essentially constant throughout the entire experimental time period of 5 h (FIG. 3b).

Example 4

Figure 4A:
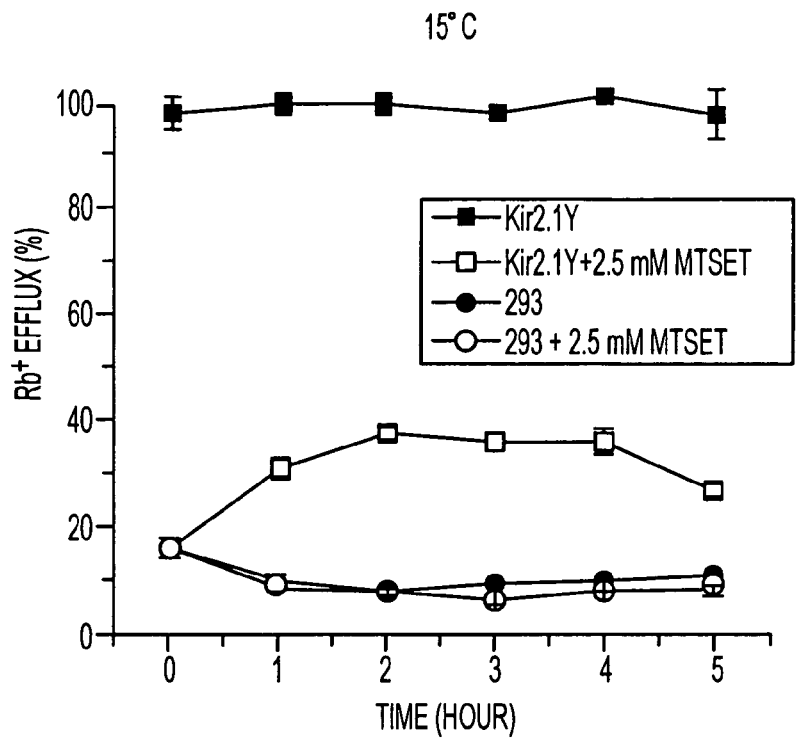
FIGS. 4a-4d. Temperature-dependent activity recovery of Kir2.1Y channel determined by $Rb^+$ efflux.
Figure 4B:
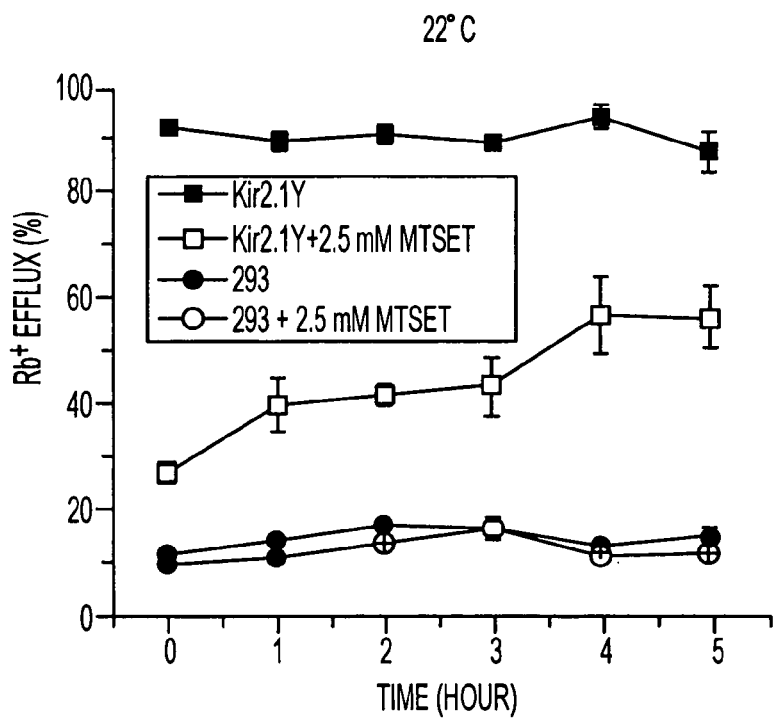
Figure 4C:
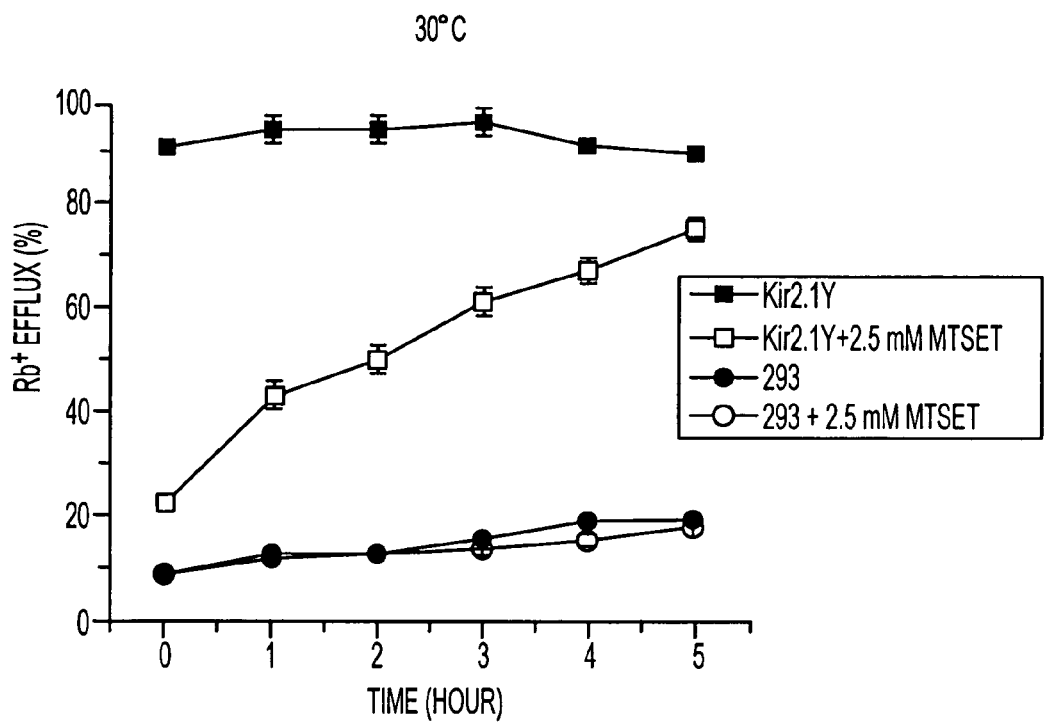
Figure 4D:
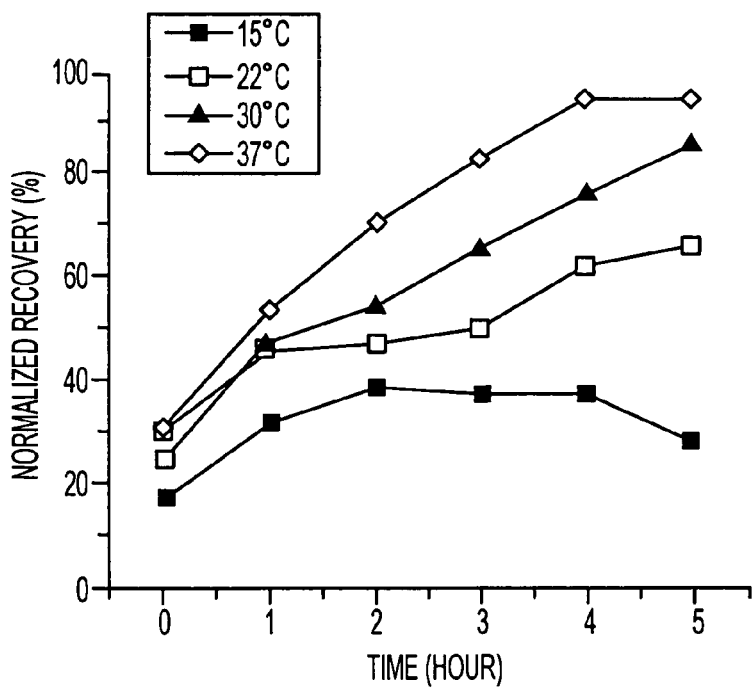

The source of functional recovery may originate from "reactivation" of the existing surface channel protein and/or from newly arrived vesicles. To test whether vesicular transport was responsible for delivering the recovered activity, the FRAC experiments were carried out in parallel but at different recovery temperatures (FIGS. 3a and 4a-4c). It is known that lowering the temperature can stall the ER-to-Golgi or cis- to trans-Golgi transitions (20). In either case, only limited recovery should be observed, presumably caused by the vesicles in transit between trans-Golgi and the cell surface. FIGS. 4a-4c shows that the recovery of activity was progressively slowed when temperatures decreased from 37° C. ($FR_{1/2}$=1 h) to 30° C. ($FR_{1/2}$=2 h) to 22° C. ($FR_{1/2}$=3.5 h). At 15° C., which typically blocks the ER-to-Golgi transition (20), the activity was recovered partially, up to 40% of the initial level (FIG. 4a). Normalized recovery suggests a residual activity at 0 h (FIG. 4d). The activity may be contributed by a rapid recovery of the functional channels during the $Rb^+$ assay, because all $Rb^+$ efflux assays were performed at 22° C. These experiments support the notion that reduction of vesicular transport at progressively lower temperatures was causal to the different $FR_{1/2}$ values.

Example 5

Vesicular trafficking is sensitive to a variety of pharmacological agents. BFA is a hydrophobic membrane-permeable fungal toxin, which was reported to inhibit multiple steps of vesicular trafficking by causing disruption of Golgi apparatus and, to some extent, ER-to-Golgi transition (21). BFA has been used to block protein secretion (22), and it is thought to act on GTP exchange factors, which activate a family of small GTPases known as ADP-ribosylation factors (23-25). Hence, the application of BFA in the above FRAC assay could test the role of vesicular transport in the recovery of channel activity on the cell surface.

Figure 5A:
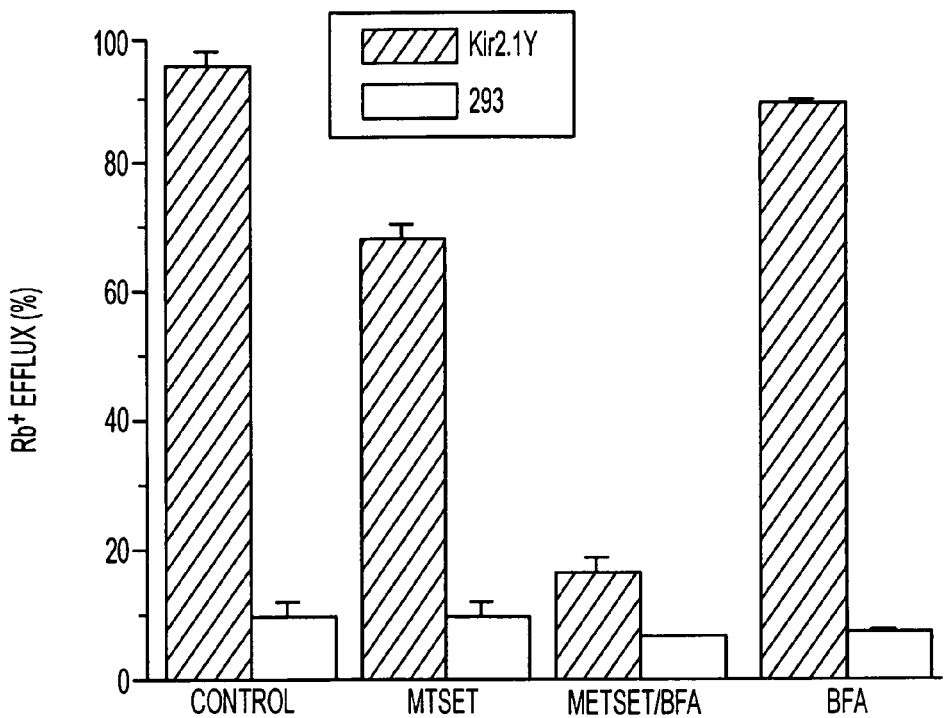
FIGS. 5a-5b. Brefeldin (BFA) effect on activity recovery of Kir2.1Y channel.

Experiments were carried out to compare the extent of activity recovery in 3 h under conditions of no treatment, MTSET only, and treatment with MTSET followed by BFA (FIG. 5a). The activity of nontreated cells remained consistent over a 3-h incubation. The MTSET-treated preparations displayed ~70% recovery, consistent with data shown in FIG. 3a. When BFA was added immediately after the MTSET treatment, <20% recovery was observed. The BFA effect was specific to the recovery because without MTSET treatment, the 3-h incubation with BFA did not affect the activity for channels that were already on the cell surface (FIG. 5a).

Figure 5B:
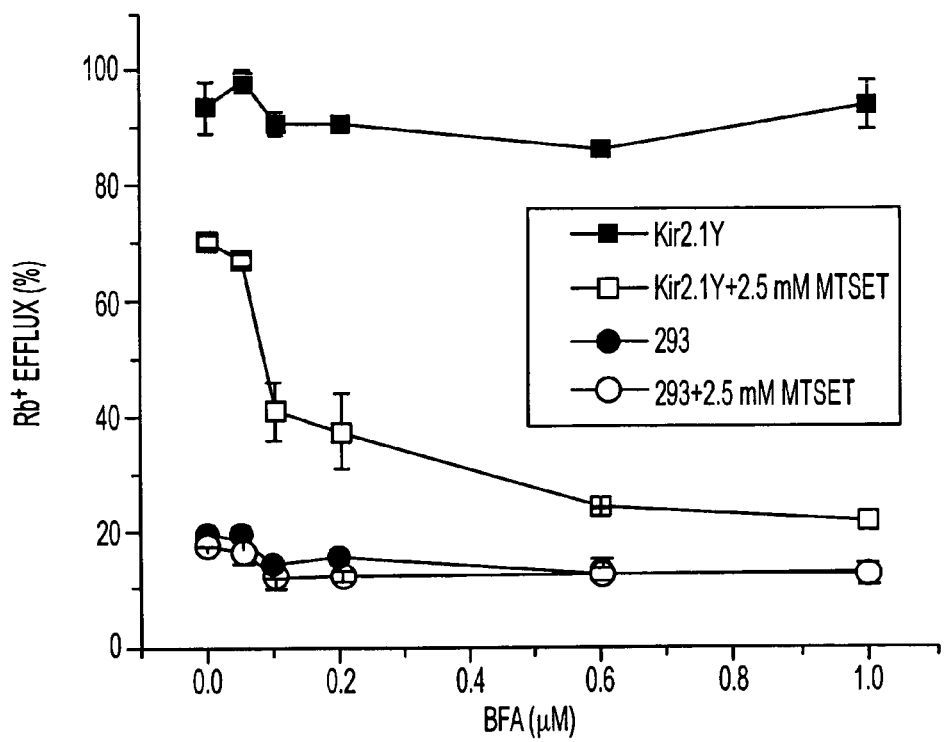

FIG. 5b shows the dose-dependent effect of BFA treatment on the recovery of activity at 3 h. The results suggest that 0.1-0.2 μM BFA treatment gave intermediate effects. Prolonged incubation with 0.2 μM BFA for up to 8 h did not yield further improvements in recovery (data not shown). The BFA effect reaches a plateau at concentrations of >0.6 μM. In the absence of MTSET treatment, the surface channel activity displayed no sensitivity to BFA concentrations (FIG. 5b), demonstrating the specificity of BFA effects for recovery.

Example 6

Incubation of BFA for the extended time of 3 h did not result in a detectable reduction of $Rb^+$ efflux activity in the absence of MTSET treatment for Kir2.1Y (FIG. 5). In the case of Kir2.1, we observed reproducible ~30% reduction over the same period of incubation (data not shown). The difference may stem from rate of endocytosis and total number of channel protein on cell surface. For Kir2.1Y, the combination of quantitative elimination of surface channel activity by MTSET, the >90% activity recovery, and little detectable reduction of $Rb^+$ efflux in the presence of BFA then would predict a 2-fold increase of protein signal on the cell surface. To the contrary, FIG. 3b provides no support of a comparable increase at the protein level. Thus, the source of the recovered activity likely originated from newly surfaced channel molecules, which represent only a small fraction of total channel protein on the cell surface. It would be particularly interesting to investigate, especially in polarized cells, any potential spatial distribution preference for the freshly replenished channel protein coupled with FRAC.

Figure 3C:
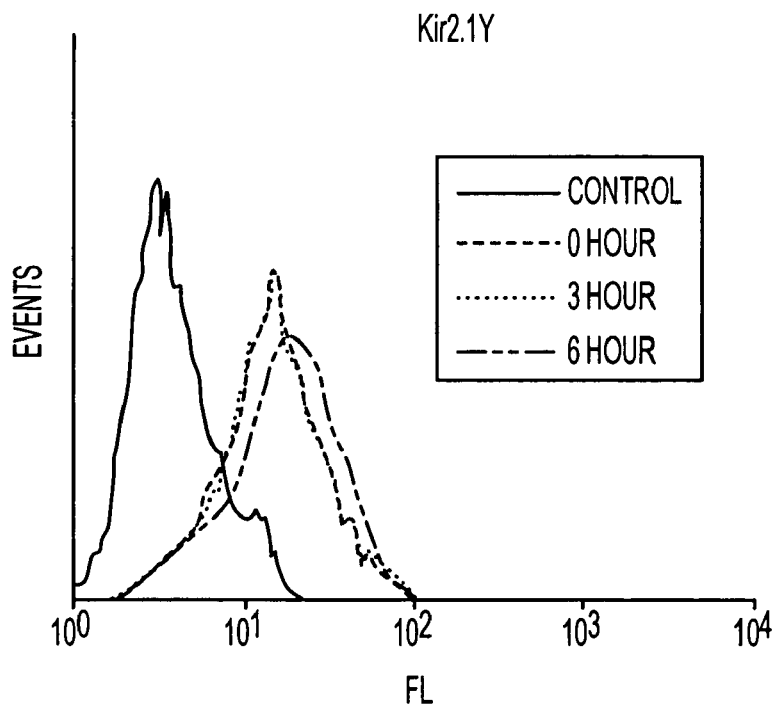

The reported method allows for a direct measurement of the transition for repopulating functional channel protein on the cell surface. Of particular interest is the observation of consistent channel activity over a long time period in the absence of ER and Golgi vesicular transport (FIG. 5a-5b). When the surfaced channel molecules were irreversibly nullified, the cells were able to repopulate the surface with newly arrived functional channels within hours. In the 3-h recovery experiments, ~70% of activity was recovered, but it was not accompanied by a significant increase of channel protein on the cell surface (FIG. 3a-3c). Together, these data provide evidence that the $Rb^+$ efflux by Kir2.1Y channels on the cell surface is contributed by only a small fraction of the channel protein, suggesting the existence of a substantial fraction of "sleeping" channels. These sleeping channels are detectable at the protein level but functionally null to the $Rb^+$ assay.

The FRAC experiments reported here allow for specific determination of the time required for a cell to populate its surface with functional channels and receptors. The electrophysiological measurement has allowed for the determination of overall conductance of the two cell lines, hence permitting an estimation of 5,000-7,000 conducting channels per cell for Kir2.1Y and 3,000-4,000 conducting channels for Kir2.1 (data not shown). It is known that different membrane proteins express with much variation in terms of molecular and functional density on the cell surface. The total recovery time likely reflects different incremental steps of biogenesis. The transit time measurement could provide a key parameter to differentiate their trafficking properties and potentially even discrete steps. For example, the fraction of BFA-insensitive recovery may represent vesicles that have exited ER and cis-Golgi compartments (FIG. 5a). Similarly, application of cycloheximide in FRAC experiments, which inhibits new protein synthesis, an earlier step than that inhibited by BFA, resulted in only 40% activity recovery (data not shown), compared with 20% activity recovery found with BFA (FIG. 5a). Hence, assays may provide resolution to isolate and evaluate compounds and cDNAs that affect these pathways, which could be useful for clinical intervention and mechanistic studies.

It is well known that cysteine substitution is a rather tolerable mutation. Site-directed mutagenesis allows for engineering a site into receptors of interest to confer sensitivity to the MTS reagent treatment (17). One can also use other covalent chemistry including various compounds that react with a primary amine group. There are certainly other available methods in addition to MTS agents that may be used to "inactivate" receptors. For example, some receptors have antagonists with extremely high affinity and/or an unusually long off-rate. Dizocilpine (MK-801) is an open channel blocker for the N-methyl-D-aspartate (NMDA) receptor. It is conceivable that MK-801 combined with a calcium-based assay would allow for determination of the rate by which NMDA receptors repopulate the neuron surface. The spatial resolution of $Ca^{2+}$-based imaging technologies may offer a comparison of rates for recovery in different subcellular domains of a single cell.

Of the >400 ion channel genes in the human genome, at least 167 are annotated to encode $K^+$ channels. $K^+$ channels are critical to a variety of biological processes ranging from neuronal excitability to oncogenesis. High-throughput assays to monitor channel activities and trafficking are of great value (15). Recently, a few cardiac $K^+$ channels, particularly human ether-ago-go-related gene (hERG)-encoded $K^+$ channels, have become subjects of recommended safety testing for all drug candidates, because many approved drugs have been found to inhibit hERG, which causes acquired long QT syndrome. These include therapeutic agents such as antiarrhythmics, antihistamines, antipsychotics, and antibiotics (26). The interactions of some of these compounds with the HERG $K^+$ channels prolong cardiac repolarization, hence QT prolongation (long QT). In some cases, long QT induces torsade de pointes, which potentially could cause cardiac sudden death (27). The activity of HERG channels can be monitored by the $Rb^+$ assay (28). There is an increasing demand of profiling compounds' effect on HERG channel activity in earlier stages of drug development. The reported assay should be useful to provide insights into possible roles of these drugs and candidate compounds in affecting the trafficking of the HERG channel protein.

REFERENCES

The disclosure of each reference cited is expressly incorporated herein.
1. Pfeffer, S. (2003) *Cell* 112, 507-517.
2. Ellgaard, L. & Helenius, A. (2003) *Nat. Rev. Mol. Cell. Biol.* 4, 181-191.
3. Mellman, I. & Warren, G. (2000) *Cell* 100, 99-112.
4. Ma, D. & Jan, L. Y. (2002) *Curr. Opin. Neurobiol.* 12, 287-292.
5. Blanpied, T. A., Scott, D. B. & Ehlers, M. D. (2003) *Neurobiol. Aging* 24, 1095-1104.
6. Wieland, F. T., Gleason, M. L., Serafini, T. A. & Rothman, J. E. (1987) *Cell* 50, 289-300.
7. Nishimura, N. & Balch, W. E. (1997) *Science* 277, 556-558.
8. Merlie, J. P. & Lindstrom, J. (1983) *Cell* 34, 747-757.
9. Bonifacino, J. S. & Glick, B. S. (2004) *Cell* 116, 153-166.
10. Axelrod, D., Ravdin, P., Koppel, D. E., Schlessinger, J., Webb, W. W., Elson, E. L. & Podleski, T. R. (1976) *Proc. Natl. Acad. Sci. USA* 73, 4594-4598.
11. Edidin, M., Zagyansky, Y. & Lardner, T. J. (1976) *Science* 191, 466-468.
12. Reits, E. A. & Neefjes, J. J. (2001) *Nat. Cell Biol.* 3, E145-E147.
13. Shikano, S. & Li, M. (2003) *Proc. Natl. Acad. Sci. USA* 100, 5783-5788.
14. Yang, J., Jan, Y. N. & Jan, L. Y. (1995) *Neuron* 15, 1441-1447.
15. Xu, J., Chen, Y. & Li, M. (2004) *Targets* 3, 32-38.
16. Zhou, B. Y., Ma, W. & Huang, X. Y. (1998) *J. Gen. Physiol.* 111, 555-563.
17. Karlin, A. & Akabas, M. H. (1998) *Methods Enzymol.* 293, 123-145.
18. Kubo, Y., Yoshimichi, M. & Heinemann, S. H. (1998) *FEBS Lett.* 435, 69-73.
19. Terstappen, G. C. (1999) *Anal. Biochem.* 272, 149-155.
20. Saraste, J. & Kuismanen, E. (1984) *Cell* 38, 535-549.
21. Lippincott-Schwartz, J., Yuan, L. C., Bonifacino, J. S. & Klausner, R. D. (1989) *Cell* 56, 801-813.
22. Sciaky, N., Presley, J., Smith, C., Zaal, K. J. M., Cole, N., Moreira, J. E., Terasaki, M., Siggia, E. & Lippincott-Schwartz, J. (1997) *J. Cell Biol.* 139, 1137-1155.
23. Chardin, P. & McCormick, F. (1999) *Cell* 97, 153-155.
24. Jackson, C. L. & Casanova, J. E. (2000) *Trends Cell Biol.* 10, 60-67.
25. Nebenfuhr, A., Ritzenthaler, C. & Robinson, D. G. (2002) *Plant Physiol.* 130, 1102-1108.
26. De Ponti, F., Poluzzi, E. & Montanaro, N. (2000) *Eur. J. Clin. Pharmacol.* 56, 1-18.
27. Antzelevitch, C. & Shimizu, W. (2002) *Curr. Opin. Cardiol.* 17, 43-51.

We claim:
1. A method of measuring the recovery of a function on a cell surface, comprising:
    treating the cell surface with a chemical or biological agent to affect an activity of a first population of cell surface receptors located on the surface of the cell at time of treating, whereby the activity is changed from a first to a second state wherein the receptors are potassium channels and wherein the chemical or biological agent is a methanethiosulfonate;
    detecting the first state of the activity on the cell surface to determine presence of a second population of the cell surface receptors, wherein the second population is not present on the cell surface at the time of treating, wherein the amount or rate of appearance of the second population of the cell surface receptors provides a measure of the recovery.

2. The method of claim 1 wherein said method is performed on the cell surface of a first and a second type of cells, wherein the first type of cell is from a pathological sample and the second type of cell is from a normal sample.

3. The method of claim 1 wherein said method is performed on the cell surface of a first and a second type of cells, wherein the first type of cells is a genetically modified version of the second type of cells.

4. The method of claim 1 wherein prior to the step of treating, the cell surface is treated with a test compound, and the effect of the test compound on recovery of the first state of the activity is determined.

5. The method of claim 2 wherein the first type of cell is a cancer cell.

6. The method of claim 1 wherein the first type of cell is a heart cell.

7. The method of claim 3 wherein the first type of cells carries a mutation in a gene encoding the cell surface receptors.

8. A method of evaluating a test compound for its effect on the recovery of a function on a cell surface, comprising:
    incubating the cell in the presence of the test compound;
    treating the surface of the cell with a chemical or biological agent to affect an activity of a first population of cell surface receptors located on the surface of the cell at time of treating, whereby the activity is changed from a first to a second state;
    detecting the first state of the activity on the surface of the cell to determine presence of a second population of the cell surface receptors, wherein the second population is not present on the cell surface at the time of treating.

9. The method of claim 8 wherein the effect of the test compound on the recovery of the first state of activity is determined by comparing to a control cell which has not been incubated in the presence of the test compound.

10. The method of claim 1 wherein the cell surface receptors are native to the cell.

11. The method of claim 1 wherein the cell surface receptors are recombinant.

12. The method of claim 1 wherein the cell surface receptors are mutant.

13. The method of claim 1 wherein the cell surface receptors are wild-type.

14. The method of claim 1 wherein the cell surface receptors are homogeneous within the first population.

15. The method of claim 1 wherein the cell surface receptors are heterogeneous within the first population.

16. The method of claim 1 wherein the cell surface receptors bind to a ligand in the first state but do not bind to the ligand in the second state.

17. The method of claim 1 wherein the cell surface receptors bind to a ligand in the second state but do not bind to the ligand in the first state.

18. The method of claim 1 wherein the first and second states differ in magnitude of the activity of the cell surface receptors.

19. The method of claim 1 wherein the activity of the cell surface receptors in the first state is greater than the activity of the cell surface receptors in the second state.

20. The method of claim 1 wherein the activity of the cell surface receptors in the first state is less than the activity of the cell surface receptors in the second state.

21. The method of claim 1 wherein the cell surface receptors are Kir2.1 channels.

22. The method of claim 1 wherein the cell surface receptors are Kir2.1Y channels.

23. The method of claim 1 wherein the first state of the activity is detected using a $Rb^+$ flux assay.

24. The method of claim 1 wherein the activity is detected by electrophysiological recording.

25. The method of claim 1 wherein the activity is detected by spectroscopy.

26. The method of claim 1 wherein a chemical agent is used in the step of treating and the chemical agent covalently modifies the cell surface receptor.

27. The method of claim 1 wherein the step of treating irreversibly affects the activity of the first population of cell surface receptors.

28. The method of claim 1 wherein the step of treating employs 2-(trimethylammoniumethyl)methanethiosulfonate bromide.

29. The method of claim 8 wherein the step of incubating precedes the step of treating.

30. The method of claim 8 wherein step of treating precedes the step of incubating.

31. The method of claim 8 further comprising:
determining if the step of incubating delays the presence of the second population on the cell surface.

32. The method of claim 1 wherein the step of detecting is performed at a predetermined time.

33. The method of claim 1 wherein the step of detecting is repeated to determine a rate of appearance of activity of the second population on the cell surface.

34. The method of claim 1 wherein the cell surface receptor is a pore-forming channel which has six membrane-spanning segments and a first, a second, and a third extracellular domain.

35. The method of claim 1 wherein the first state of the activity of the cell surface receptor is detected using a first antibody.

36. The method of claim 35 wherein the first antibody is radiolabeled.

37. The method of claim 35 wherein the first antibody is fluorescently labeled.

* * * * *